(12) United States Patent
Rosenheimer

(10) Patent No.: US 6,595,930 B2
(45) Date of Patent: Jul. 22, 2003

(54) PROBE FOR PHYSIOLOGICAL PRESSURE MEASUREMENT IN THE HUMAN OR ANIMAL BODY AND METHOD FOR MONITORING THE PROBE

(75) Inventor: Michael N. Rosenheimer, Oberschweinbach (DE)

(73) Assignee: MIPM Mannendorfer Institut fur Physik und Medizin GmbH (DE)

( * ) Notice: Subject to any disclaimer, the term of this patent is extended or adjusted under 35 U.S.C. 154(b) by 0 days.

(21) Appl. No.: 10/002,254

(22) Filed: Oct. 26, 2001

(65) Prior Publication Data

US 2002/0091327 A1 Jul. 11, 2002

(51) Int. Cl.⁷ ................................................ A61B 5/00
(52) U.S. Cl. ...................... 600/561; 600/300; 600/549; 600/555; 600/587
(58) Field of Search ................................ 600/300, 549, 600/555, 561, 585, 587

(56) References Cited

U.S. PATENT DOCUMENTS

| | | | | |
|---|---|---|---|---|
| 4,204,547 A | | 5/1980 | Allocca | 128/748 |
| 4,858,615 A | * | 8/1989 | Meinema | 128/897 |
| 5,247,938 A | * | 9/1993 | Silverstein et al. | 600/459 |
| 5,359,993 A | * | 11/1994 | Slater et al. | 600/133 |
| 5,383,874 A | * | 1/1995 | Jackson et al. | 606/1 |
| 5,425,375 A | * | 6/1995 | Chin et al. | 600/549 |
| 5,437,284 A | * | 8/1995 | Trimble | 600/486 |
| 6,237,604 B1 | * | 5/2001 | Burnside et al. | 128/897 |
| 6,241,679 B1 | * | 6/2001 | Curran | 600/485 |
| 6,266,551 B1 | * | 7/2001 | Osadchy et al. | 600/424 |
| 6,298,255 B1 | * | 10/2001 | Cordero et al. | 600/372 |

FOREIGN PATENT DOCUMENTS

| | | |
|---|---|---|
| DE | 374 1833 C1 | 4/1989 |
| DE | 196 54 724 C2 | 4/1998 |

* cited by examiner

*Primary Examiner*—Robert L. Nasser
*Assistant Examiner*—Patricia Mallari
(74) *Attorney, Agent, or Firm*—St. Onge Steward Johnston & Reens LLC

(57) ABSTRACT

A probe for physiological pressure measurement in a human or animal body comprises a probe head, a line such as a catheter, and a pressure transducer, particularly an electric transducer, in the probe head. For measuring pressure, the probe head with the pressure transducer is disposed at a measuring site for pressure measurement, with the probe head being adapted for connection to an analyzer and display unit via the line. A counter or controller means is provided for recording a number of operational applications of the probe.

45 Claims, 3 Drawing Sheets

PROBE FOR PHYSIOLOGICAL PRESSURE MEASUREMENT IN THE HUMAN OR ANIMAL BODY AND METHOD FOR MONITORING THE PROBE

TECHNICAL FIELD

The present invention relates to a probe for physiological tonometry or pressure measurement in a human or animal body, the probe comprising a probe head, a line such as a catheter, and a pressure transducer in the probe head. For measuring pressure in the body, the probe head with the pressure transducer is disposed at the measuring site, with the probe head being adapted to be connected to an analyzer and display unit via the line.

BACKGROUND OF THE INVENTION

Probes of this kind have been known for a long time and are employed particularly for intra-cranial pressure measurement. There, the probe consists of a probe head including an electric pressure transducer. For tonometric measurement, the probe head with the pressure transducer is arranged on the measuring site. The probe head is then connected via a catheter including electric connecting leads to an analyzer and display unit by means of a coupler such as a connector. The pressure measured by the probe or detected by the pressure transducer included in the probe head is then displayed in the display unit.

Such probes may be used mainly to measure the epidural pressure—in this case the probe is located between the cranial bones and the Dura mater—the subdural pressure—here the probe is located between the Dura mater and the brain substance—the parenchymatous pressure—for this measurement the probe is located in the brain substance—or the ventricular pressure—in which case the probe is located in a ventricle. All of these measurements are consistently measurements of a relative pressure, which means that the pressure is measured relative to the environment.

The pressure transducer consists, for instance, of a piezo crystal mounted on the distal end of the catheter in the probe head. The catheter may comprise a silicon tube or a tube made of another biologically compatible material, for example, and includes electric leads disposed inside. The catheter is adapted for connection via a coupler to the analyzer and display unit.

Resistance strain gauges or capacitive pressure transducers may also be employed as an alternative to the piezo crystal. The electric pressure transducer is designed as a bridge circuit, e.g. in the form of a Wheatstone bridge, in order to increase the sensitivity. A current or voltage source outside the probe is provided for supplying the bridge circuit or the pressure transducer with electric power. The leads are connected to a voltage source and the pressure transducer.

For tonometric application, the probe is guided to the measuring site in the body. Then the catheter is connected to the analyzer and display unit that serves equally as power or voltage source, i.e. a source of energy, for the probe. The energy and equally the electric signals are transmitted via the electric leads contained in the catheter tube. The measurement of a relative pressure requires the storage of the electric value of the bridge voltage at zero pressure. To this end, null balancing must be carried out.

The crucial point in the known probes resides, however, in the aspect that these probes are only able to perform a certain number of pressure measurements and must then be recalibrated. As a result of the necessary sterilization cycles, the users are therefore required to record a log of the number of the operating applications of the probe. When a predetermined number of operating applications of the probe—i.e. of pressure measurements—is reached, the probe must be returned to the manufacturer for recalibration.

This method of recording the performed operating applications is, however, extremely expensive and, as a rule, does not function in an optimum manner in practical application. As result, probe failure occurs again and again because the probes are used even though the specified number of operating applications has been exceeded. In the everyday routine in a hospital it is impossible to keep records of the number of operating applications. The reliability and safety in operation is then no longer ensured and failure occurs in the implanted condition, which exposes the clinically monitored patient to a substantial risk.

SUMMARY OF THE INVENTION

The present invention is therefore based on the problem of improving a probe for physiological pressure measurement in the human or animal body in such a way that a facilitated recording of the operating applications will become possible while the aforementioned disadvantages are avoided.

This problem is solved by providing a counter means which records the number of performed operational applications of the probe.

This problem can also be solved by a controller means, which records a transducer offset value after each autoclaving or sterilization operation performed to sterilize the probe after each use and detects an error condition by detecting abnormal offset values or abnormal offset value changes since a previous autoclaving or sterilization operation.

The invention is based on the finding that counter or controller means are available of such a small size that they can be incorporated into probes so that the probe can record and report its operating applications automatically.

In accordance with the present invention, the probe therefore comprises a counter or controller means recording the operating applications of the probe. In this simple manner it is ensured that each tonometric application will be recorded. Now a record kept by hand is no longer required. Moreover, this provision improves the safety with respect to manipulations of the specified number of operating applications and hence the documentability of possibly asserted warranty claims.

In a preferred embodiment at least one additional counter for counting overload conditions of the pressure transducer is integrated in the unit. It can be set to count overload conditions all the time during autoclaving or sterilization or only during regular operation.

In another preferred embodiment an additional counter for counting autoclaving or sterilization operation is provided. These autoclaving or sterilization operations may be detected by a rise in temperature or pressure.

Another preferred embodiment of the invention comprises an additional timer for measuring operational hours.

The counter means is preferably disposed in that part of the coupler that is connected to the line.

In order to prevent specifically any use of the probe in excess of the specified number of operational uses and hence false measuring results or the failure of the probe during measurement, the counter means renders the pressure transducer and hence the probe inoperative as soon as the specified number of operating applications is reached.

The number of the operating applications and/or the number of applications remaining until the end of service of the probe can be displayed via a display means so that the user can inform himself at any time about the remaining number of operational applications and the number of completed operational uses of the probe. To this end, the display means is integrated, in particular, into that part of the coupler that is connected to the line so that the user can obtain this information from the probe directly.

According to one embodiment of the invention, the probe comprises an electric pressure transducer and an electric counter means. The counter means is configured with temperature-resistant electric components. The counter means triggers a counting operation only when voltage is applied to the probe throughout a defined period. This provision is intended to prevent that the counting operation is triggered when a voltage is applied only briefly. This may be the case, for instance, when the connection with the probe is to be tested. What is to be counted is only the occurrence of an actual application in operation, i.e. when the voltage is applied, for instance, for half an hour at minimum.

To prevent a further use of the probe when the specified number of operating applications has already been reached, the counter means operates a switch that disconnects the power supply of the pressure converter when a specified number of operational applications is reached. The analyzer and display unit recognizes this situation and stops the measurement or no longer permits a further measurement. This prevents a further application of the probe in operation. The user is hence forced in a simple manner to return the probe to the manufacturer for inspection and calibration.

The counter means preferably operates in a decrementing mode for rendering the probe inoperative, i.e. it counts from the specified number down to zero so that when zero is reached the probe is taken out of service. Additionally, the counter means operates continuously in an incrementing mode for recording the total number of operational applications of the probe. The user is thus enabled, on the one hand, to detect the total number of applications of the probe and, on the other hand, to establish the number of potential operating applications remaining up to the point where the probe is rendered inoperative and the probe must be inspected and calibrated by the manufacturer.

To ensure small dimensions of the probe and to widen the range of potential applications even further, the counter means comprises a microprocessor with a memory, with the number of operating applications as well as the remaining number of potential operating applications up to the end of service being stored in this memory.

According to one embodiment of the invention, the display means is constituted by a light-emitting diode that indicates the desired number by a string of flashing signals. With this provision, the smallest display means possible is implemented.

Preferably the number of the specified operational applications of the probe can be set. This number is set in particular when the specified number of operating applications is reached, at which the probe is rendered inoperative, and at the time when the service is resumed after calibration. The setting is carried out by means of appropriate software.

In order to be able to handle maintenance jobs in a facilitated manner the memory stores further data such as manufacturer-specific information such as serial number, customer number, date of delivery, name of the person calibrating the probe, date of last calibration, or the like.

The blood-borne Creutzfeld-Jakob (CFJ) disease has occurred recently to an increasing extent. Insofar it is necessary to use methods for sterilization which operate at temperatures higher than 130° C. in order to ensure a complete and safe destruction of the CFJ agents. The probe therefore consists of a biologically compatible material stable in terms of temperature, which allows a sterilization method such as autoclaving/steam sterilization above 130° C. As far as is known to date, the CFJ agents are completely destroyed at these temperatures, which permits repeated use of the probe.

A particular field of application of this probe is that of intra-cranial pressure measurement. For this application a small size—preferably a diameter less than 8 mm is required. With a drop-shaped housing the explantation is simplified significantly.

Another preferred embodiment of the invention comprises a controller which detects an error condition by comparing an offset value by at least on predetermined limit value. So the offset value can be compared for example with an upper limit value and a lower limit value. If it is outside the limit values an error condition occurs.

For improved detection of error conditions a value like the first order derivation which is a measure of change of offset values is calculated. This may be done by subtracting an offset value of a previous offset value and dividing the difference by a value which is either the number of operational/calibration cycles or the time elapsed between the measurement of these values. An error condition may be detected by comparing such a value by at least on predetermined limit value. By this way extreme, abnormal changes of the offset value can be detected.

For further improved detection the previous procedure can be applied to the change of offset values themselves to get a second order derivation. This can also be compared by predetermined limit values.

A method for monitoring lifetime and reliability of pressure probes is described. This method uses a probe head, a line such as a catheter, and a pressure transducer in the probe head. The number of operational applications of the probe are counted.

A method for monitoring lifetime and reliability of pressure probes is described. This method uses a probe head, a line such as a catheter, and a pressure transducer in the probe head. The offset value of the pressure transducer is measured after each sterilization operation or before each new application of the probe. The offset value, changes of offset values, changes of changes of offset values are evaluated to detect error conditions or states of abnormal operation.

BRIEF DESCRIPTION OF THE DRAWINGS

Further advantages and features of the invention become evident from the following description of an embodiment of the invention with reference to the drawings wherein.

DETAILED DESCRIPTION OF THE PREFERRED EMBODIMENTS

Figure 1:
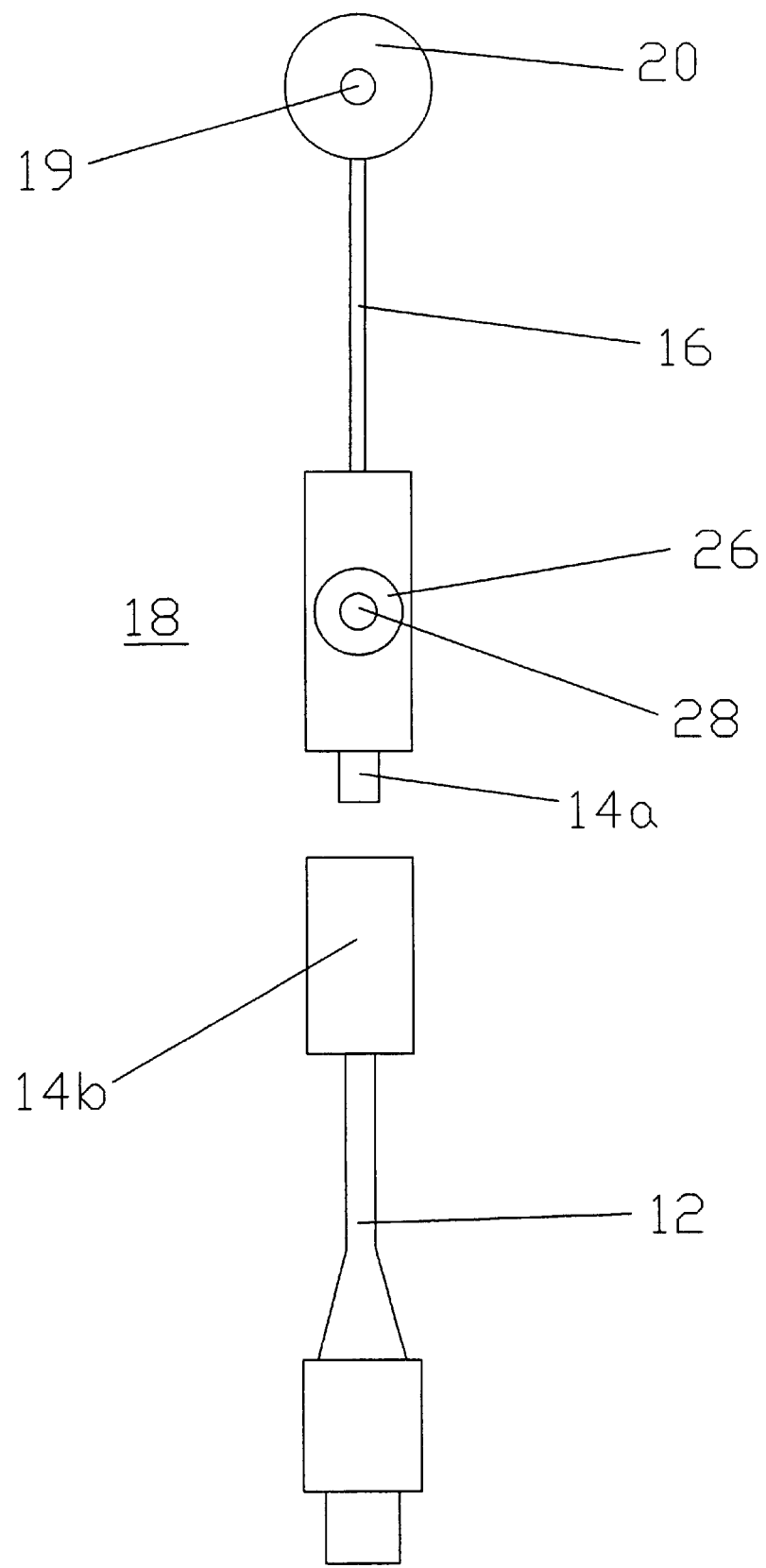
FIG. 1 is a schematic view of the inventive probe including a connecting cable.

In the drawings reference numeral 30 is alternatively related to the counter or controller. The physical arrangement of counter and controller could be at the same positions although their functions are different.

Figure 2:
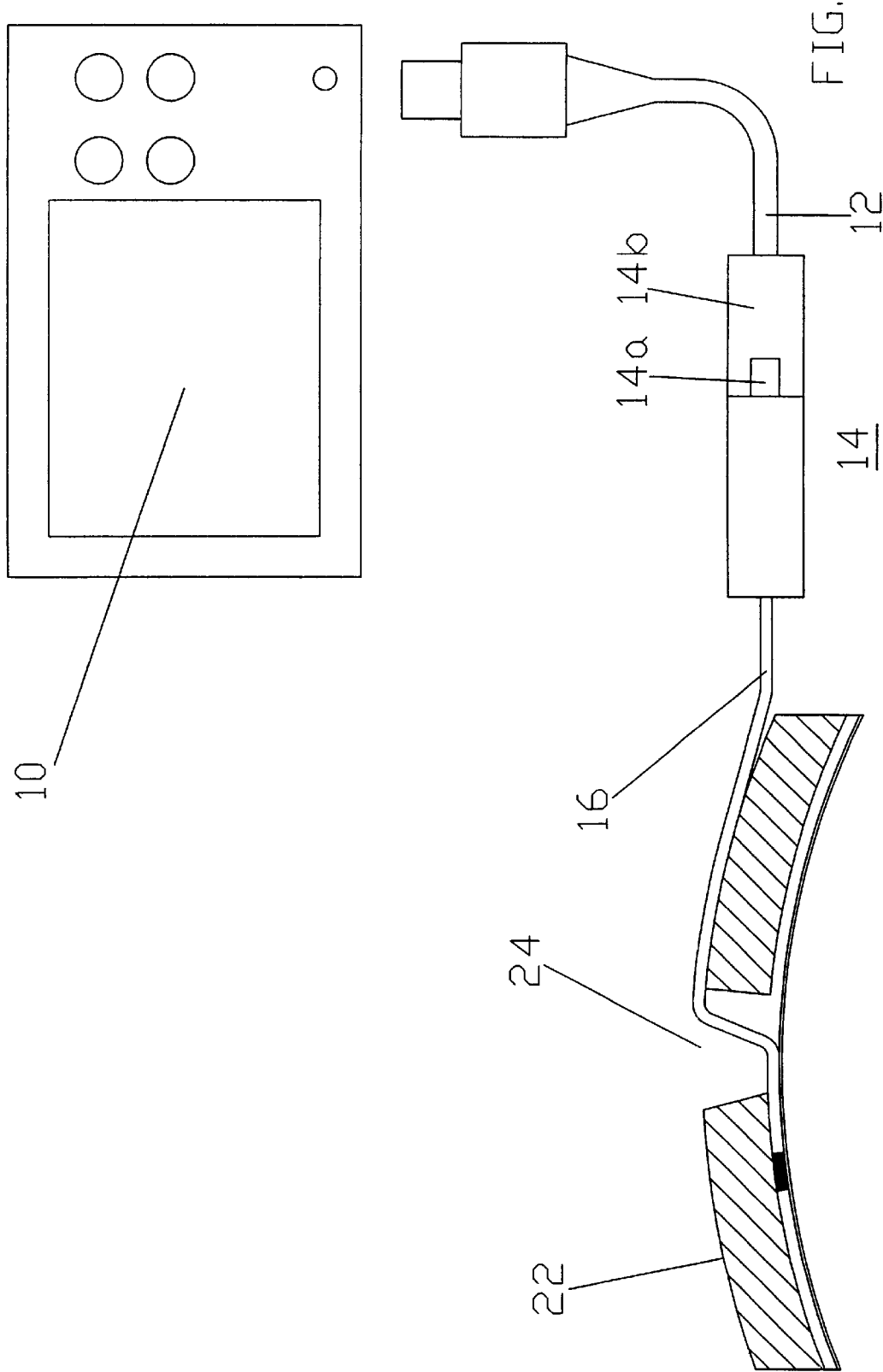
FIG. 2 shows a schematic illustration of the measurement of cerebral pressure, using the probe of FIG. 1.

FIG. 1 shows a probe 18 according to the present invention while FIG. 2 is a schematic illustration of a display and analyzer unit 10 for intra-cranial pressure measurement. A connecting cable 12 is connected to this unit 10 and, via a plug connector 14 which serves as coupler, to a catheter 16. A probe head 20 is disposed on the distal end of the catheter 16. The probe head 20 is inserted via an opening 24 into a patient's skull 22. The probe head 20 is located here between the Dura mater and the cranial bones for measuring the epidural pressure.

The probe 18 comprises a piezo crystal as pressure transducer, together with a bridge circuit, in a manner known per se. The bridge circuit is supplied with power via leads extending within the catheter 16, with the unit 10 serving as energy source.

A window 26 is formed in the connector 14 to permit an unobstructed view of a light-emitting diode 28 inside the connector 14.

Figure 3:
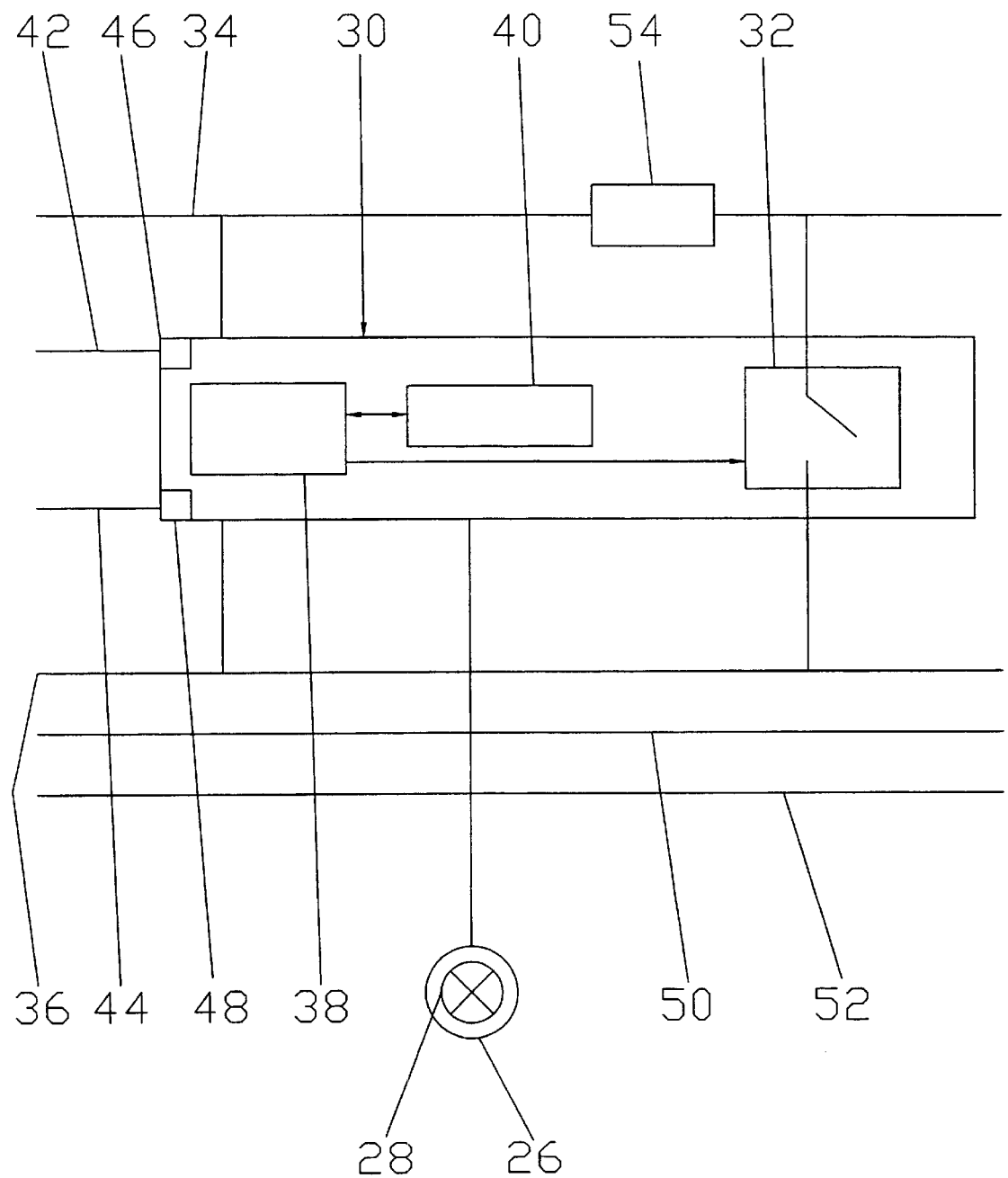
FIG. 3 is a block diagram of the counter means of the probe according to FIG. 1.

FIG. 3 is a schematic block diagram illustrating components inside the part 14b of the connector 14.

A counter/controller means 30, which cooperates with the light-emitting diode 28 and a switch 32, is connected to the input side of the bridge circuit. The counter/controller means 30 is connected to the energy source of the bridge circuit via line 34 and via line 36. Alternatively a controller means can be used instead of the counter means.

A voltage supplied by the energy source serves to operate a microprocessor 38 that cooperates with a memory 40. The microprocessor 38 and the memory 40 are parts of the counter means 30 disposed inside the part 14b of the connector 14. The counter/controller means 30 comprises moreover data lines 42 and 44 connected to a data input 46 and a data output 48. A predetermined number is input into the counter/controller means 30 via the data lines, and when this number is reached the switch 32 is actuated.

The predetermined number is set by means of a computer. The measuring signals of the bridge circuit are transmitted via the lines 50 and 52 to the unit 10.

Prior to the start of operation of the probe 18, a predetermined number is input via the data lines 42 and 44 into the counter/controller means 30, for instance twenty operational applications. Furthermore, a period is specified via the data lines 42 and 44, from which onwards a respective counting operation is to be performed. For example, when a voltage is applied to the lines 34 and 36 for at least half an hour, a counting operation is triggered.

The counter/controller means 30 hence counts the number of operational applications, i.e. the pressure measurements, of the probe 18. An operational application is then defined in such a way that a voltage must be applied to the lines 34 and 36 for at least half an hour. When the voltage has been applied for more than half an hour a counting operation is triggered. The counting operation then decrements from the specified number one unit at a time, so that the number of remaining operational applications is stored in the memory 40. Furthermore, the total number of operational applications is detected, which means that after each operational application the number is incremented by one and then separately stored in the memory 40.

The number of operational applications still remaining up to actuation of the switch 32 is indicated by a string of flashing signals via the light-emitting diode 28.

The switch 32 is illustrated in FIG. 3 in a state in which the probe has not yet reached the predetermined number of operational applications. As soon as the specified number of operating applications is reached the switch 32 is closed to short the lines 34 and 36. With this switching the bridge circuit is rendered inoperative and the probe 18 can no longer be used for tonometric applications.

The user must then return the probe 18 to the manufacturer for calibration.

After calibration, the manufacturer sets anew the specified number via the setting means 42 and 44, so that the switch 32 will be opened again and the probe 18 is switched again into its state ready for operation.

The counter/controller means 30 moreover comprises a data input 46 and a data output 48 via which the contents of the memory 40 can be read, which means that the manufacturer can establish how often the probe 18 has been in operation altogether and how often calibration has been performed. Apart therefrom, additional data is stored in the memory 40, specifically the customer number, the serial number, the data of delivery, the name of the person calibrating the probe 18 and the data of calibration, the date of last calibration of the probe, and similar information.

The predetermined number of the counter/controller means 30 may be set and the operation of the probe 18 resumed via the data lines 42 and 44 and the data input 46 and the data output 48, with the switch 32 then resuming its open position illustrated in FIG. 3.

A series resistor 54 is inserted in line 34—plus—so that the monitor of the display and analyzer unit 10 will not be affected.

The probe 18 is made of a temperature-resistant and biologically compatible material and is adapted for complete autoclaving, together with the catheter 16.

The invention ensures in a simple manner that an electric counter/controller means 30 with small dimensions can be realized in the probe 18, via which the predetermined number of operational applications is indicated. The switch 32 serves to prevent the probe 18 from being operative beyond the specified number of operating applications.

List of Reference Numerals 10 analyzer and display unit
12 connecting cable
14 connector
14a socket
14b plug
16 catheter
18 probe
19 pressure transducer
20 probe head
22 cranium (skull)
24 cranial opening
26 window
28 light-emitting diode
30 counter/controller
32 switch
34 line-plus
36 line-ground
38 microprocessor
40 memory
42 data line
44 data line
46 data input
48 data output
59 signal line
52 signal line
54 series resistor

What is claimed is:

1. Probe for physiological pressure measurement in a human or animal body, comprising a probe head, a line, and a pressure transducer in the probe head, said probe head with said pressure transducer being disposed at a measuring site for measuring pressure, with said probe head being adapted for connection to an analyzer and display unit via said line, characterized in that a counter means is provide which records a number of operational applications of the probe, and characterized in that the counter means has additional means for monitoring and counting overload conditions of the pressure transducer.

2. Probe according to claim 1, characterized in that the pressure transducer is an electric transducer which generates an electrical output dependent on a pressure applied to the pressure transducer.

3. Probe according to claim 1, characterized in that said counter means renders said pressure transducer and hence the probe inoperative when a specified number of operational applications has been performed.

4. Probe according to claim 3, characterized in that said counter means actuates a switch as soon as said specified number of operational applications is reached, which switch stops a supply of energy to said pressure transducer, thus preventing any further operation of the probe in an application.

5. Probe according to claim 3, characterized in that for rendering the probe inoperative, said counter means counts by decrementing from said specified number so that when zero is reached the operation of the probe is stopped.

6. Probe according to claim 1, characterized in that a coupler is provided for connection of said analyzer and display unit, and that said counter means is disposed in a part of said coupler which is connected to said line.

7. Probe according to claim 1, characterized in that the counter means has additional means for measuring a time of operation of the pressure transducer.

8. Probe according to claim 1, characterized in that the number of operational applications and/or a number of operational applications remaining up to the end of service of the probe can be displayed via a display means which is connected to said line.

9. Probe according to claim 1, characterized by an electric pressure transducer and an electric counter system that triggers a counting operation as soon as a voltage is applied to the probe throughout a predetermined period.

10. Probe according to claim 1, characterized by a configuration adapted for autoclaving.

11. Probe according to claim 1, characterized by a configuration for intra-cranial pressure measurement.

12. Probe according to claim 1, characterized in that for recording the total number of performed operational applications of the probe, said counter means operates in a continuous incrementing mode.

13. Probe according to claim 1, characterized in that said counter means includes a microprocessor with a memory.

14. Probe according to claim 13, characterized in that said memory stores the number of performed operational applications as well as a number of operational applications remaining up to an end of service of the probe.

15. Probe for physiological pressure measurement in a human or animal body, comprising a probe head, a line, and a pressure transducer in the probe head, said probe head with said pressure transducer being disposed at a measuring site for measuring pressure, with said probe head being adapted for connection to an analyzer and display unit via said line, characterized in that a counter means is provide which records a number of operational applications of the probe, characterized in that the number of operational applications and/or a number of operational applications remaining up to the end of service of the probe can be displayed via a display means which is connected to said line, and characterized in that said display means is constituted by a light-emitting diode that indicates said numbers by a string of flashing signals.

16. Probe according to claim 1, characterized in that a number of specified operating applications is settable.

17. Probe for physiological pressure measurement in a human or animal body, comprising a probe head, a line, and a pressure transducer in the probe head, said probe head with said pressure transducer being disposed at a measuring site for measuring pressure, with said probe head being adapted for connection to an analyzer and display unit via said line, characterized in that a counter means is provided which records a number of operational applications of the probe, and characterized in that the counter means has additional means for monitoring and counting a number of autoclaving or sterilization operations to which said probe has been subjected by detecting a rise in pressure.

18. Probe according to claim 13, characterized in that further data is stored in said memory.

19. A method for lifetime and reliability monitoring of pressure probes used in physiological pressure measurement in a human or animal body, using a probe head, a line, and a pressure transducer, in the probe head, characterized in that a counter means records a number of operational applications of the probe, and characterized in that the counter means monitors and counts a number of autoclaving or sterilization operations to which said probe has been subjected by detecting a rise in pressure.

20. A method for lifetime and reliability monitoring of pressure probes used in physiological pressure measurement in a human or animal body, using a probe head, a line, and a pressure transducer, in the probe head, characterized in that a controller means records a transducer offset value after each of a number of autoclaving or sterilization operations to which said probe has been subjected and detects an error condition by detecting abnormal offset values or abnormal offset value changes since a previous autoclaving or sterilization operation.

21. Probe for physiological pressure measurement in a human or animal body, comprising a probe head, a line, and a pressure transducer, in the probe head, said probe head with said pressure transducer being disposed at a measuring site for measuring pressure, with said probe head being adapted for connection to an analyzer and display unit via said line, characterized in that a controller means is provided which records a transducer offset value after each of a number of autoclaving or sterilization operations to which said probe has been subjected and detects an error condition by detecting abnormal offset values or abnormal offset value changes since a previous autoclaving or sterilization operation.

22. Probe according to claim 21, characterized in that a counter means is provided which records a number of operational applications of the probe.

23. Probe according to claim 21, characterized in that the pressure transducer is an electric transducer which generates an electrical output dependent on a pressure applied to the pressure transducer.

24. Probe according to claim 21, characterized in that the controller means has additional means for monitoring and counting overload conditions of the pressure transducer.

25. Probe according to claim 21, characterized in that the controller means has additional means for monitoring and counting said number of autoclaving or sterilization operations.

26. Probe according to claim 21, characterized in that the controller means has additional means for measuring a time of operation of the pressure transducer.

27. Probe according to claim 21, characterized in that a coupler is provided for connection of said analyzer and display unit, and that said controller means is disposed in a part of said coupler which is connected to said line.

28. Probe according to claim 21, characterized in that said controller means renders said pressure transducer and hence the probe inoperative when an error condition has been detected.

29. Probe according to claim 21, characterized in that offset values and/or error conditions of the probe can be displayed.

30. Probe according to claim 21, characterized by an electric pressure transducer and a controller which is triggered to perform an offset measurement as soon as a voltage is applied to the probe throughout a predetermined period.

31. Probe according to claim 21, characterized in that said controller means actuates a switch as soon as an error condition is detected, which switch stops a supply of energy to said pressure transducer, thus preventing any further operation of the probe in an application.

32. Probe according to claim 21, characterized in that said controller means comprises a microprocessor or microcontroller with a memory.

33. Probe according to claim 32, characterized in that a counter means is provided which records a number of operational applications of the probe and said memory stores said number as well as a number of operational applications remaining up to the end of service of the probe.

34. Probe according to claim 33, characterized in that a display means constituted by a light-emitting diode that indicates said number by a string of flashing signals, is provided.

35. Probe according to claim 33, characterized in that a specified number of operating applications to be performed is settable.

36. Probe according to claim 32, characterized in that further data is stored in said memory.

37. Probe according to claim 21, characterized by a configuration adapted for autoclaving.

38. Probe according to claim 21, characterized by a configuration for intra-cranial pressure measurement.

39. Probe according to claim 21, characterized in that the controller detects abnormal offset values by comparing the offset values by at least one predetermined limit value.

40. Probe according to claim 21, characterized in that the controller calculates offset value changes by calculating the difference between an offset value and a previous offset value.

41. Probe according to claim 40, characterized in that the controller detects abnormal offset value changes by comparing the offset value change with at least one predetermined limit value or previous offset value changes.

42. Probe according to claim 40, characterized in that the controller calculates changes of offset value changes by calculating the difference between an offset change value and a previous offset change value.

43. Probe according to claim 42, characterized in that the controller detects an error condition by comparing the change of offset value change with at least one predetermined limit value or previous change of offset value changes.

44. A method for lifetime and reliability monitoring of pressure probes used in physiological pressure measurement in a human or animal body, using a probe head, a line, and a pressure transducer in the probe head, characterized in that at least after each of a number of autoclaving or sterilization operations to which said probe has been subjected a controller unit detects errors by detecting abnormal offset values or abnormal offset value changes since a previous autoclaving or sterilization operation.

45. A method for lifetime and reliability monitoring of pressure probes used in physiological pressure measurement in a human or animal body, using a probe head, a line, and a pressure transducer, in the probe head, characterized in that a counter counts a number of operational applications of the probe, and characterized in that the counter monitors and counts overload conditions of the pressure transducer.

* * * * *